(12) United States Patent
Schneider et al.

(10) Patent No.: US 8,661,921 B2
(45) Date of Patent: Mar. 4, 2014

(54) SENSING APPARATUS FOR GROUND SENSING FROM THE INTERIOR OF A VEHICLE, AND VEHICLE HAVING SUCH A SENSING APPARATUS

(75) Inventors: Lars Schneider, Naumburg (DE); Hartmut Wagner, Reinholterode (DE)

(73) Assignee: Krauss-Maffei Wegmann GmbH & Co. KG (DE)

( * ) Notice: Subject to any disclaimer, the term of this patent is extended or adjusted under 35 U.S.C. 154(b) by 150 days.

(21) Appl. No.: 13/259,140

(22) PCT Filed: Jan. 5, 2010

(86) PCT No.: PCT/DE2010/000015
§ 371 (c)(1),
(2), (4) Date: Sep. 22, 2011

(87) PCT Pub. No.: WO2010/111987
PCT Pub. Date: Oct. 7, 2010

(65) Prior Publication Data
US 2012/0017705 A1 Jan. 26, 2012

(30) Foreign Application Priority Data
Apr. 1, 2009 (DE) .......................... 10 2009 015 828

(51) Int. Cl.
*G01N 1/24* (2006.01)
(52) U.S. Cl.
USPC ....................................................... 73/864.73
(58) Field of Classification Search
None
See application file for complete search history.

(56) References Cited

U.S. PATENT DOCUMENTS

| | | | |
|---|---|---|---|
| 3,464,504 A * | 9/1969 | Stange ............................. | 173/28 |
| 3,841,973 A | 10/1974 | Wilkins et al. | |
| 4,982,616 A | 1/1991 | Koch et al. | |
| 5,437,203 A | 8/1995 | Koch et al. | |
| 5,629,201 A | 5/1997 | Nutgeren et al. | |
| 6,116,097 A | 9/2000 | Berglund et al. | |
| 6,260,633 B1 * | 7/2001 | Machek et al. ................. | 175/20 |
| 7,628,059 B1 * | 12/2009 | Scherbring ....................... | 73/84 |
| 2002/0007687 A1 | 1/2002 | Zimmermann et al. | |

FOREIGN PATENT DOCUMENTS

| | | |
|---|---|---|
| DE | 9100367.9 | 5/1991 |
| DE | 29604341 | 6/1996 |
| DE | 19712420 | 9/1998 |
| DE | 29910714 | 6/2000 |
| EP | 0982471 | 3/2000 |
| WO | WO93/24609 | 12/1999 |

* cited by examiner

*Primary Examiner* — Robert R Raevis
(74) *Attorney, Agent, or Firm* — Jennifer Stachniak; Berenbaum Weinshienk PC

(57) ABSTRACT

A sensing apparatus for ground sensing from the interior of a vehicle, comprising a sensing probe capable of being brought into contact with the ground, and a handle for moving the sensing probe from a rest position into a lower ground sensing position. The sensing probe can be coupled with the handle such that upon actuation of the handle, the sensing probe is lowered into the ground sensing position accompanied by lever action. A lowering locking mechanism can be provided for arresting a lowering movement of the sensing probe. For orientation purposes, the sensing probe can be pivotable via the handle about an essentially horizontal pivot plane, and an orientation arresting mechanism can be provided for arresting an orientation position of the sensing probe. In a vehicle having such a sensing apparatus, the sensing probe can be guided through the bottom of the interior of the vehicle.

9 Claims, 14 Drawing Sheets

SENSING APPARATUS FOR GROUND SENSING FROM THE INTERIOR OF A VEHICLE, AND VEHICLE HAVING SUCH A SENSING APPARATUS

The instant application should be granted the priority dates of Apr. 1, 2009, the filing date of the corresponding German patent application 10 2009 015 828.6, as well as Jan. 5, 2010, the filing date of the International patent application PCT/DE2010/000015.

BACKGROUND OF THE INVENTION

The present invention relates to a sensing apparatus for ground sensing from the interior of a vehicle, including a sampling, or sensing, probe that can be brought into contact with the ground, and a handle for moving the sampling probe from an idle or rest position into a lowered ground sensing position, as well as to a vehicle having such a sensing apparatus.

Sensing apparatus for ground sensing are utilized with, in particular military, detection vehicles in order to be able to identify, for example, noxious materials and warfare agents in the ground, and hence in the environment. In this connection, the ground sample can be taken up and analyzed in solid form by means of a grabber arm or in a volatilized form.

One known detection vehicle having a tong-like gripper arm is described, for example, in DE 91 00 367 U1. To collect ground samples, disposed in the rear region is a sample receiving apparatus in which are disposed various devices, such as a tongs, by means of which the ground samples can be collected from the ground and accommodated in a sample receiving container that can then be closed and safely transported to a laboratory. The detection vehicle is furthermore provided with a dual wheel sensing apparatus having a mass spectrometer. During the detection process with the known mass spectrometer, it is necessary during the trip, with the aid of the dual wheel detection apparatus, to transport contaminations that have possibly deposited upon the ground, with the aid of a silicone hose disposed on the detection wheel, and for the detection to convey it further to the mass spectrometer. A dual wheel detection device for ascertaining warfare agents is also described in DE 84 24 372 U1.

It is furthermore known from the military detection tank of the "fox" type to undertake a ground analysis via a detection apparatus, embodied as a detection lance, disposed in the rear portion of the vehicle. For this purpose, there is a manually operable detection probe that can be operated from the interior of the armored vehicle. The detector here has a long tube that is guided through the rear vehicle wall. By means of a short grip as a handle on one end of the detection probe, the detector can position the detection probe and can apply the pressure necessary for carrying out the ground analysis. Disposed at the other end of the detection probe is a detection or sensing head that contains a heating element, so that the ground sample can volatilize. These ground vapors are then guided through the tubular detection lance into the interior of the vehicle to an analysis device.

A drawback with the state of the art is that it is not possible to ergonomically carry out an operation due to the long tube. Furthermore, a great amount of force must be applied in order to achieve the pressure necessary for carrying out the ground detection. Due to the construction, the arrangement must be accommodated in a roomy rear end, where in addition the detecting process is observable through a glass viewing block in the rear wall.

It is an object of the present invention to embody a sensing apparatus, and a vehicle having a sensing apparatus, in such a way that a convenient operability is achieved for the detector individual.

SUMMARY OF THE INVENTION

Pursuant to a first inventive embodiment, the sensing prove is coupled with the handle in such a way that upon actuation of the handle, the sensing probe is lowered into the ground sensing position accompanied by lever action. Due to the lever action, the introduction of force for achieving the necessary pressure can be significantly improved. Pursuant to one preferred embodiment, the handle has a rocker-type configuration. In this way, a straightforward construction of the handle for achieving the lever action is achieved. The handle is preferably pivotably coupled with the sensing probe, in particular via a ball-and-socket joint. In this way, despite the lever action it is possible to achieve a nearly vertical lowering of the sensing probe. The lowering can thus be effected with the aid of lever force.

To achieve a lever action, the handle preferably includes a lever and a lever support. Pursuant to a particularly advantageous embodiment, the handle includes a one-hand pull lever that is supported by the lever support. By means of the one-hand pull lever, an ergonomically advantageous configuration of the handle can be achieved.

Pursuant to a preferred embodiment, the lever support can be connected with the vehicle by means of a support bracket mechanism, which can be configured such that, for the orientation of the sensing probe, pivot movements of the sensing probe can be carried out about an essentially horizontal pivot plane. Thus, the sensing probe can be pivoted about a pivot point disposed in the pivot plane. If the sensing probe has a tubular or rod-shaped configuration, the pivot plane can be disposed essentially perpendicular to the axis of the tube or rod. As a consequence of these lateral orientation movements, the detector can locate a spot within a sensing zone that is suitable for the ground sensing without the vehicle having to carry out any ranging movements.

For this purpose, the support bracket mechanism can, in particular, include a pivot bearing that in particular has an essentially vertical axis of rotation. In addition, the support bracket mechanism can include an in particular essentially horizontal linear guide. As a consequence of the combination of pivot bearing and horizontal linear guide, a large orientation zone can be achieved for the sensing probe.

Pursuant to a second inventive embodiment, the sensing apparatus is configured in such a way that the lowering movement of the sensing probe can be arrested by means of a lowering locking mechanism. By means of the lowering locking mechanism, a convenient operability results for the detector individual, since different lowering positions can be fixed in a defined manner. In this connection, the lowering locking mechanism can include an apertured plate into which engages a pin that is connected with the handle and which is movable relative to the apertured plate for the arresting action.

The lowering locking mechanism is preferably releasable by means of a lowering release actuation mechanism that is disposed on the handle. This facilitates the one-hand operation of the sensing apparatus. The sensing probe can preferably be arrested in the rest position or in the ground sensing position.

Furthermore, the sensing probe, between the rest position and the ground sensing position, can also be arrested in an air sensing position and/or a head-changing position. In the air sensing position, the sensing head is not in contact with the ground. By means of the sensing head, a sample of the ambient air is taken and is conveyed into the vehicle to an analysis device. In the head-changing position, the sensing head is also not in contact with the ground. However, it permits a simple exchange or replacement, which can then be necessary, for example, if a contamination has been established.

Due to the defined arrested positions of the sensing probe, a sensor can additionally be utilized for sensing the rest or idle position, the ground sensing position, the air sensing position and/or the head-changing position. A straightforward configuration results if the sensor is disposed directly on the lowering locking mechanism and thus senses the individual arrested positions. As a consequence of the sensing, various positions of the sensing probe can be indicated to the detector and also to a driver of the sensing or detection vehicle. In addition, it is possible, for example by means of a control device, to prevent the vehicle from departing if the sensing probe is disposed in the ground sensing position, thus reducing the danger of an accident and damage.

Pursuant to a third inventive embodiment, the sensing apparatus is configured in such a way that for orientation purposes, the sensing probe is pivotable via the handle about an essentially horizontal pivot plane, whereby the orientation position can be arrested by means of an orientation arresting mechanism. Thus, the sensing probe can be pivoted about a pivot point disposed in the pivot plane, and in particular can be pivoted in a ball-and-socket jointed manner. If the sensing probe has a tubular or rod-shaped configuration, the pivot plane can be disposed essentially perpendicular to the axis of the tube or rod. The advantages of a sensing probe that can be oriented have already been described.

By means of the orientation arresting mechanism, the orientation position can be arrested, so that after orientation has been completed, no further lateral orientation movements are permitted by means of the orientation arresting mechanism, so that then the once oriented sensing probe need merely be lowered into the ground sensing position.

The orientation arresting mechanism can preferably be releasable by means of an orientation release actuation mechanism disposed on the handle. This once again facilitates the one-hand operability of the sensing apparatus.

An inventive vehicle having an already described sensing apparatus is configured such that the sensing probe is guided through the interior bottom of the vehicle. Due to the fact that the sensing probe is now no longer guided through a rear wall of the vehicle, shorter lowering paths result. Furthermore, the ergonomics can be improved such that a nearly vertical lowering movement can be achieved. In this connection, the sensing probe can be connected with the vehicle via a ball insert having a passage, by means of which, in conjunction with the ball-and-socket joint support of the sensing probe in the handle, the pivot movements for the orientation of the sensing probe, and axial movements for the lowering and raising of the sensing probe, are permitted.

The sensing probe preferably includes a tubular section, on one end of which is disposed a sensing head. Furthermore, a compartment can be disposed below the vehicle through which the sensing probe is guided. In addition, in the rest position, the sensing head can be arranged in the compartment, which can preferably be closed off, thus resulting in a protected rest or idle position of the sensing head.

Since the sensing apparatus is utilized in particular in military vehicles, which are generally provided with a special protection against mines, it will not be possible to directly follow the ground sensing process, which takes place below the vehicle, from the interior of the vehicle. For this reason, a camera can be disposed below the vehicle, by means of which the sensing process can be observed by means of an indicator or display unit.

The sensing head preferably includes a heating element for volatilizing ground samples. In particular, the ground vapors can be conveyed through the sensing probe, especially through the tubular section, into an analysis device in the vehicle.

The ergonomic configuration of the vehicle can be further enhanced by providing, a working space for a detector individual in the interior of the vehicle, whereby the handle is disposed in the grasping zone of the detector. This avoids that for the ground sensing the detector has to leave its seat and has to move to the back of the vehicle.

Thus, the present invention can also be utilized in vehicles having small vehicle interiors.

A ground sensing position can preferably be sensed by means of a sensor, whereby the sensor is connected with a control device that, upon sensing the ground sensing position, prevents a movement of the vehicle.

All of the aforementioned inventive embodiments can be combined with one another.

BRIEF DESCRIPTION OF THE DRAWINGS

A preferred configuration of the invention will be described with the aid of FIGS. 1 to 14, in which.

DESCRIPTION OF SPECIFIC EMBODIMENTS

Figure 1:
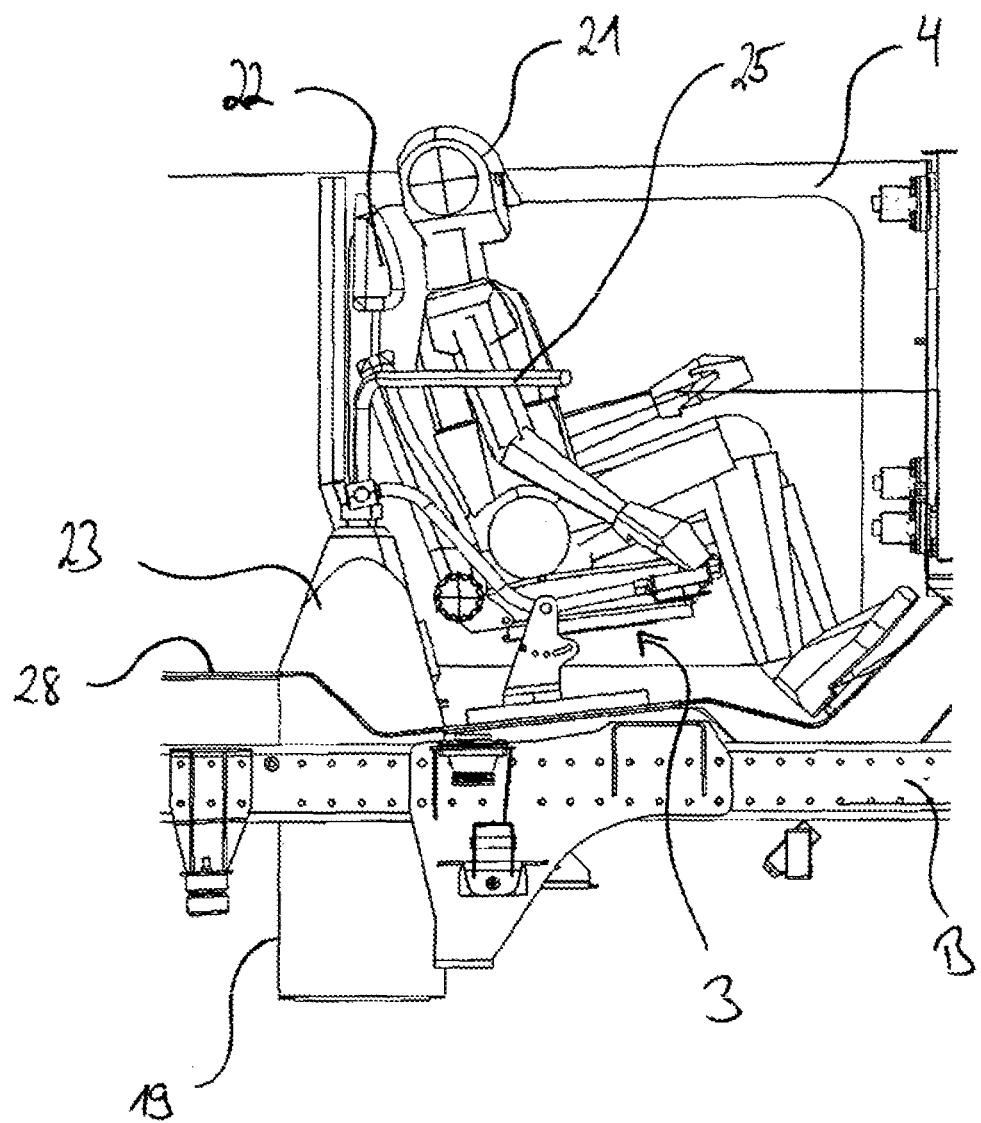
FIG. 1 is a longitudinal cross-section of a vehicle having a sensing apparatus in the rest or idle position.
Figure 2:
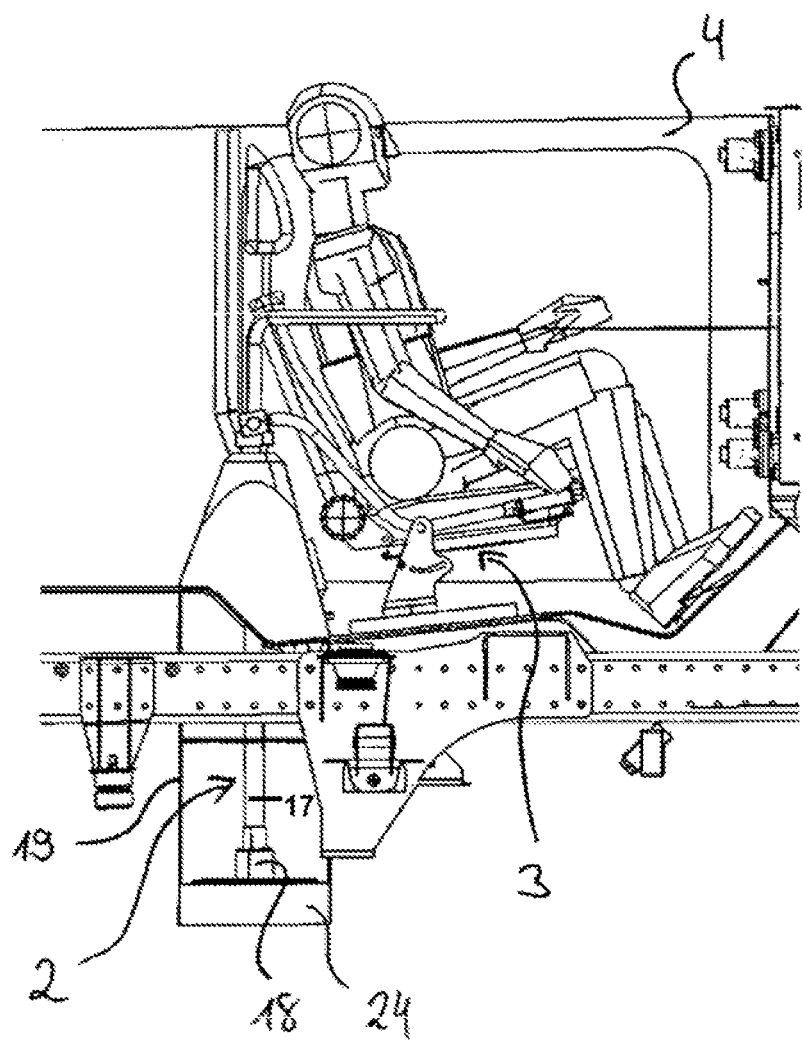
FIG. 2 shows the vehicle of FIG. 1 with partially transparent elements.
Figure 14:
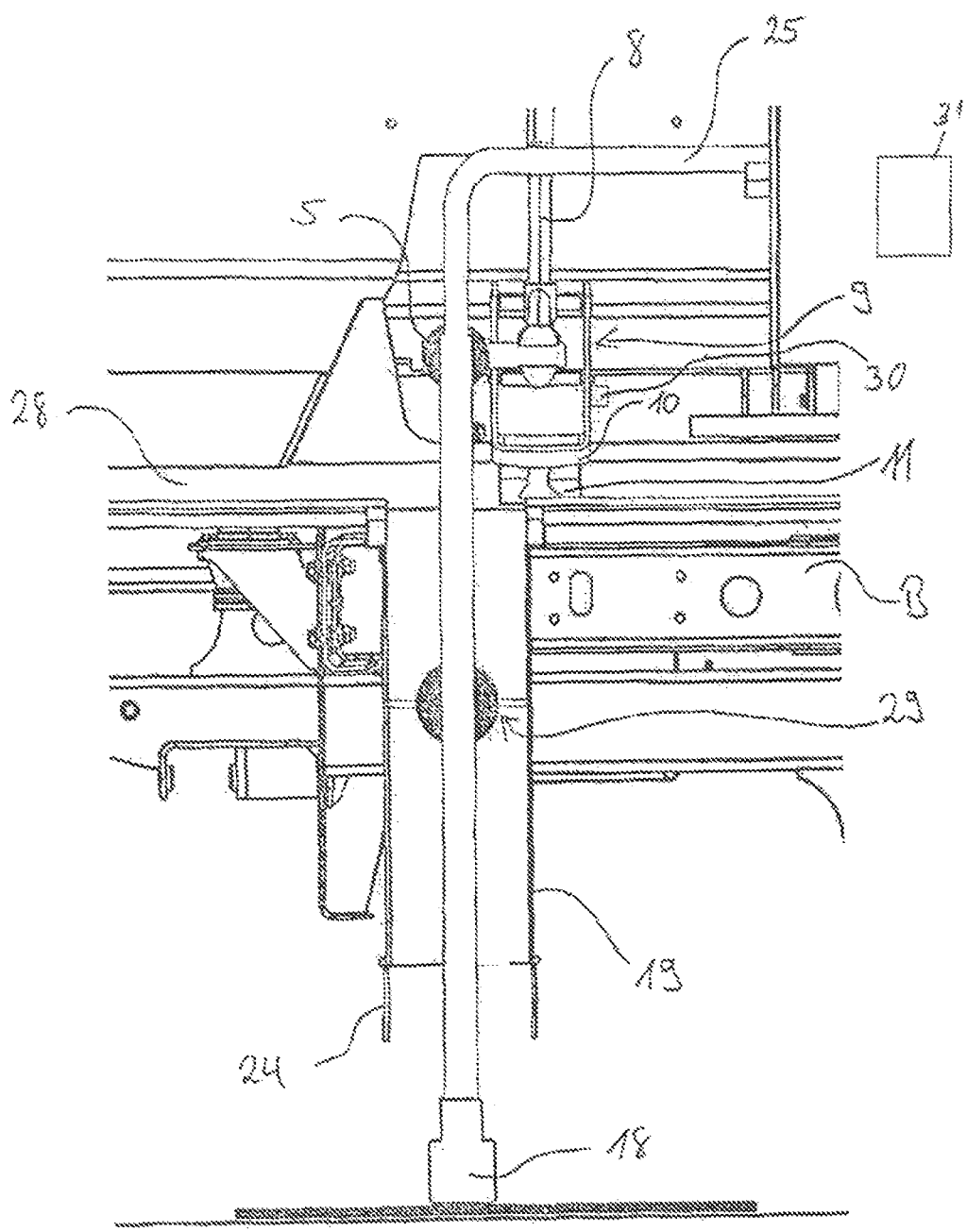
FIG. 14 is an enlarged transverse sectional illustration of the end of the sensing apparatus of FIG. 1.

FIGS. 1 and 2 show a military vehicle 4 which, as a sensing vehicle, undertakes sensing or detecting tasks. For this purpose, a workspace of a detector 21 is provided in the interior of the vehicle 4. The vehicle 4 has a sensing apparatus 1, which includes a sensing probe 2 and a manually actuatable handle 3. The sensing probe 2 has a tubular section 17 that, by means of a support plate 29 having a ball insert with a passage (illustrated in FIG. 14), is guided through an interior bottom 28 of the vehicle and the base B of the vehicle 4.

In FIGS. 1 and 2, the sensing apparatus 1 and the sensing probe 2 are in a rest or idle position. In the idle position, the sensing head 18, which is disposed at one end of the tubular section 17, is located, in a well protected manner, entirely within the compartment 19, which is disposed below the base B of the vehicle and is shown transparent in FIG. 2. Pursuant to FIG. 1, the compartment is closed off by means of a closure mechanism 24, which can be actuated manually or by a motor; in FIG. 2, the closure mechanism 24 is opened. To protect against mines, the sensing probe 2 can be provided with a non-illustrated breaking point.

The sensing head 18 includes a non-illustrated heating element for volatilizing soil samples. The soil sample vapors are drawn through the tubular section 17 and via a corrugated tube 25 into the interior of the vehicle 4 to a non-illustrated analysis device.

Figure 6:
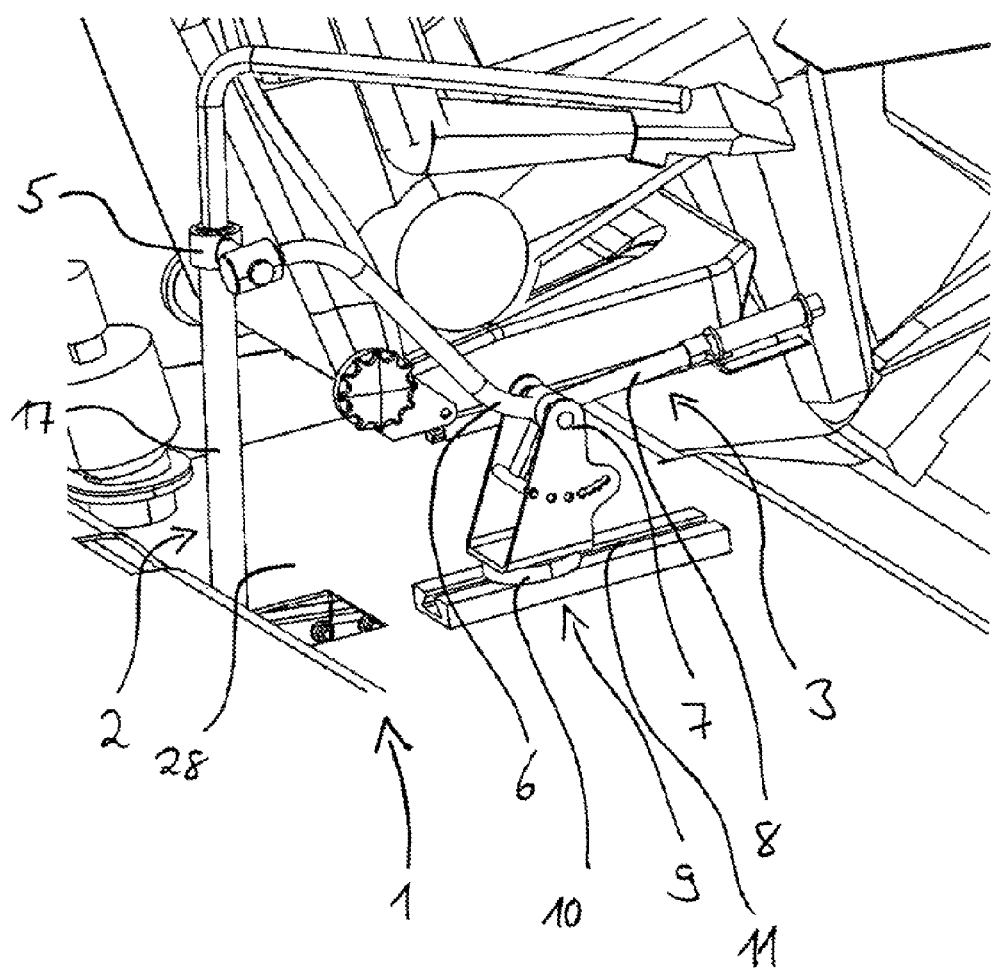
FIG. 6 shows the part of the sensing apparatus of FIG. 5 with elements partially omitted.

By means of the handle 3, the detector individual 21 can align or orient and lower the sensing probe 2. For this purpose, the handle 3 has a tilt or rocker type configuration. As shown in FIG. 6, it includes a one-hand pull lever 8, which is connected with the interior bottom 28 of the vehicle by means of a lever support 7 and a support bracket mechanism 9. Pulling on the one-hand pull lever 8 lowers the sensing probe or sampling device 2 downwardly. In this connection, the handle 3 is pivotably coupled with the sensing probe 2 via a ball-and-socket joint having a passage therethrough, so that the lever movement of the handle 3 is converted into an essentially vertical lowering movement. By means of the ball-and-socket joint 5, the sensing probe 2 can be pivoted about an essentially horizontal pivot plane H (FIG. 7), so that orientations X (FIG. 8) and Y (FIG. 12) of the sensing probe 2 and of the sensing head 18 can be achieved. The ball-and-socket joint 5 thus represents the pivot point disposed in the horizontal plane H.

The lever support 7 is configured as a bearing bracket and includes an essentially horizontal pivot axis. The lever support 7 is again connected with the interior bottom 28 of the vehicle by means of a support bracket mechanism 9, which in this connection includes on the one hand a pivot bearing 10 having a pivot axis that extends essentially perpendicular to the interior bottom 28 of the vehicle, and hence extends essentially vertically. By means of the pivot bearing 10, pivoting movements of the handle 3 can be carried out, thus enabling an orientation or placement movement of the sensing probe or lance 2, especially in a lateral direction. The support bracket mechanism 9 furthermore includes a linear guide 11, by means of which it is possible to execute a linear movement of the handle 3 that extends essentially parallel to the interior bottom 28 of the vehicle, and hence extends essentially horizontally, as a consequence of which an orientation movement of the sensing probe 2 in the longitudinal direction of the vehicle is achieved. Thus, by means of the handle 3, and via the support bracket mechanism 9, it is possible to carry out orienting pivot movements of the sensing probe 2 about a pivot plane that extends essentially parallel to the interior bottom 28 of the vehicle and hence extends essentially horizontally.

Figure 5:
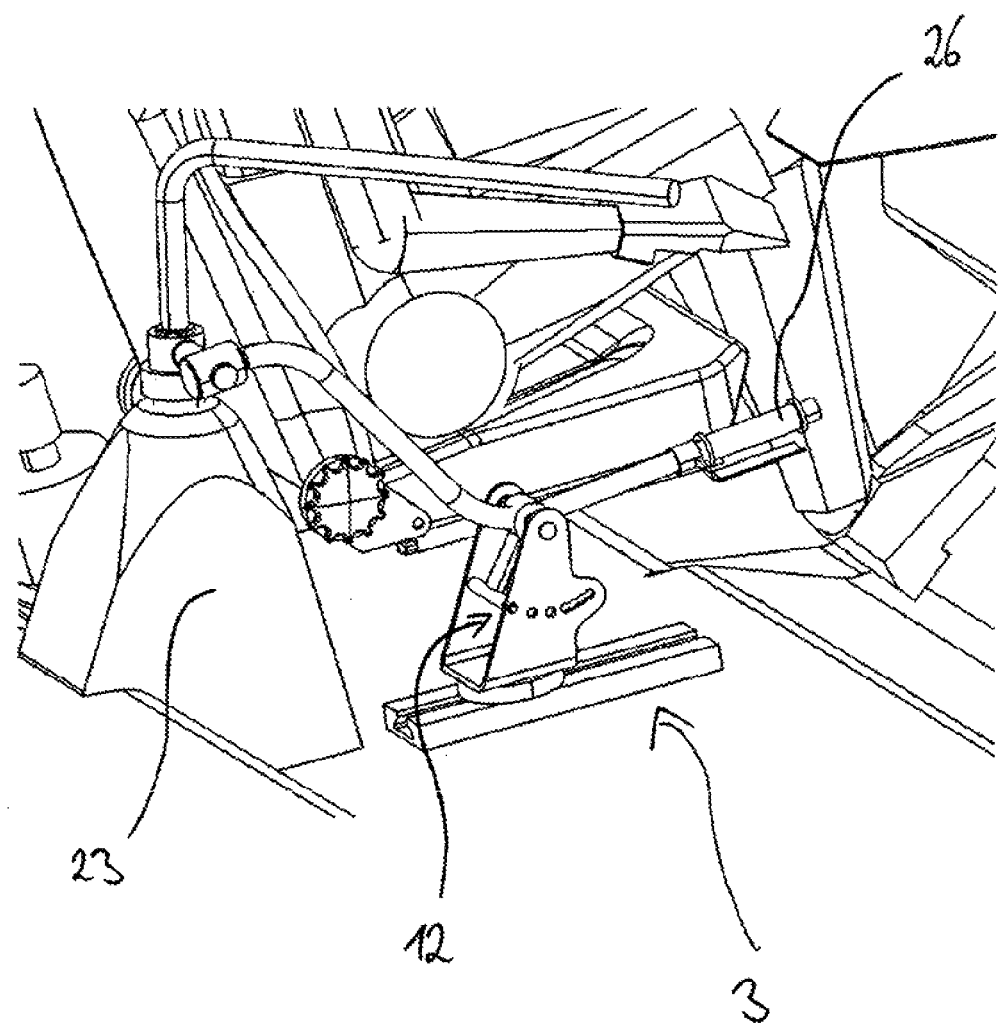
FIG. 5 is a perspective illustration of that portion of the sensing apparatus of FIG. 1 that is in the inside of the vehicle.

To prevent possibly contaminating ambient air from passing into the interior of the vehicle, as shown in FIG. 5 the guiding of the sensing probe 2 through the interior bottom 28 of the vehicle and through the base B is sealed by a rubber bellows or covering 23 that is flexibly configured such that it permits orientation and lowering movements of the sensing probe 2.

Figure 3:
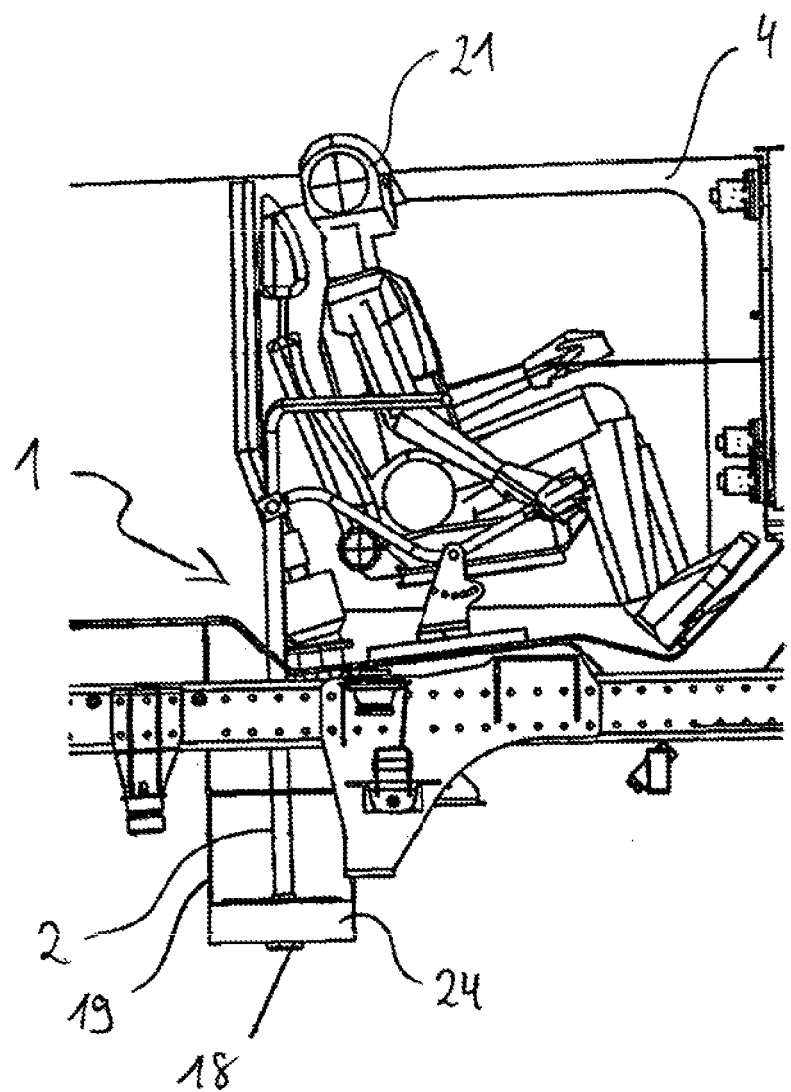
FIG. 3 shows the vehicle of FIG. 2 with the sensing apparatus in the air sensing position.

FIG. 3 shows the sensing apparatus 1 with the sensing probe 2 in an air sensing position. This position is assumed when samples of ambient air are to be collected for analysis. In the air sensing position, the sensing head 18, with the closure mechanism 24 open, extends out of the compartment 19 only to the extent necessary, thus not unnecessarily reducing the ground clearance of the vehicle. Thus, air sensing can also be carried out while the vehicle 4 is being driven.

Figure 4:
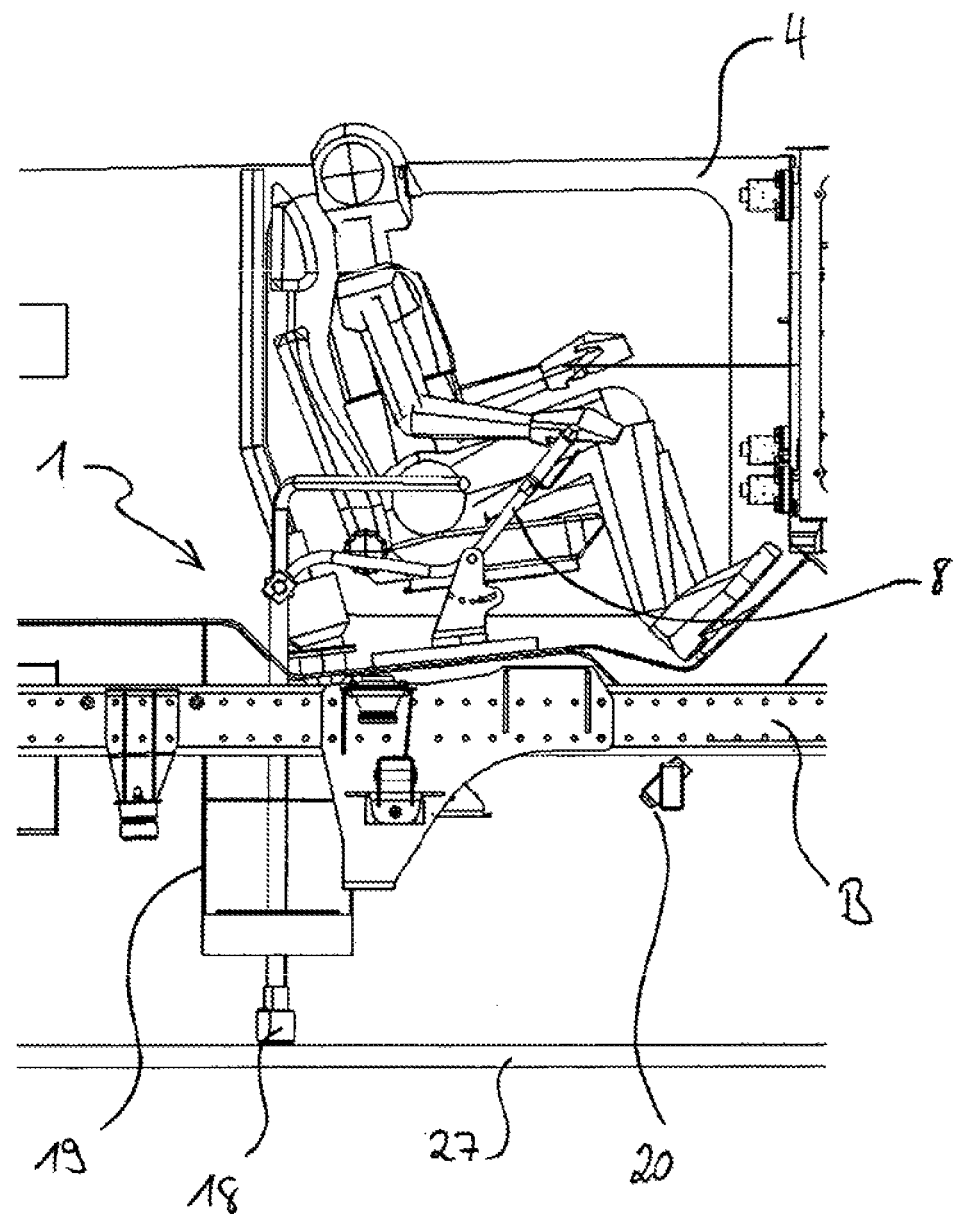
FIG. 4 shows the vehicle of FIG. 3 with the sensing apparatus in the ground sensing position.

FIG. 4 shows the sensing apparatus 1 in the ground sensing position. For this purpose, by pulling on the one-hand pull lever 8, and under lever effect, the sensing probe 2 is pressed against the ground 27, so that a ground sample can be volatilized and drawn in.

Figure 7:
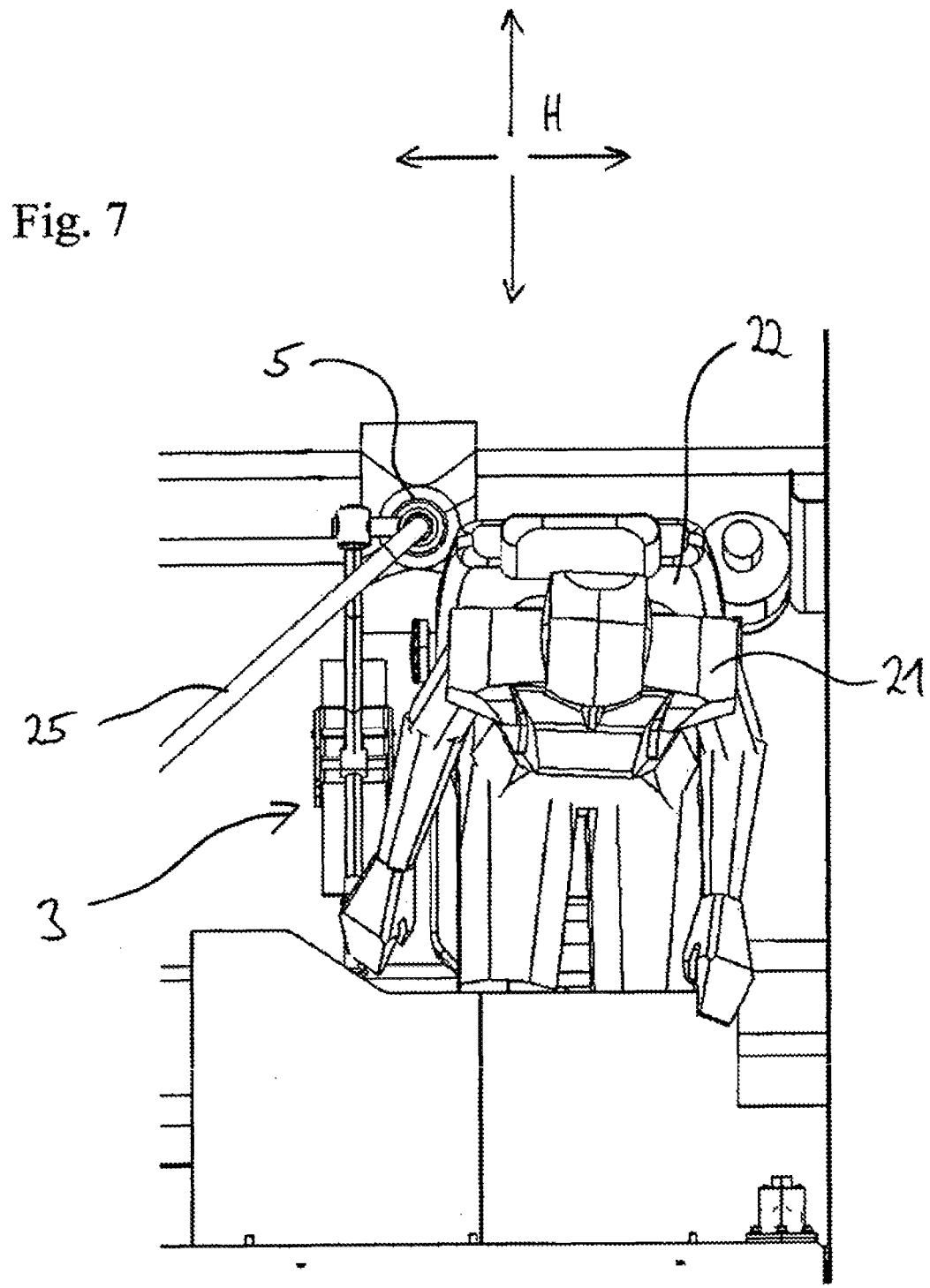
FIG. 7 is a plan view of the working space of a detector individual in the vehicle of FIG. 1.

FIG. 7 is a plan view showing the working space of the detector 21. The handle 3 is disposed next to the seat 22 of the detector within the grasping zone of the detector. The arrangement of the handle next to the seat 22 is thus comparable to the arrangement known for parking brakes (hand brake) in passenger vehicles.

Figure 8:
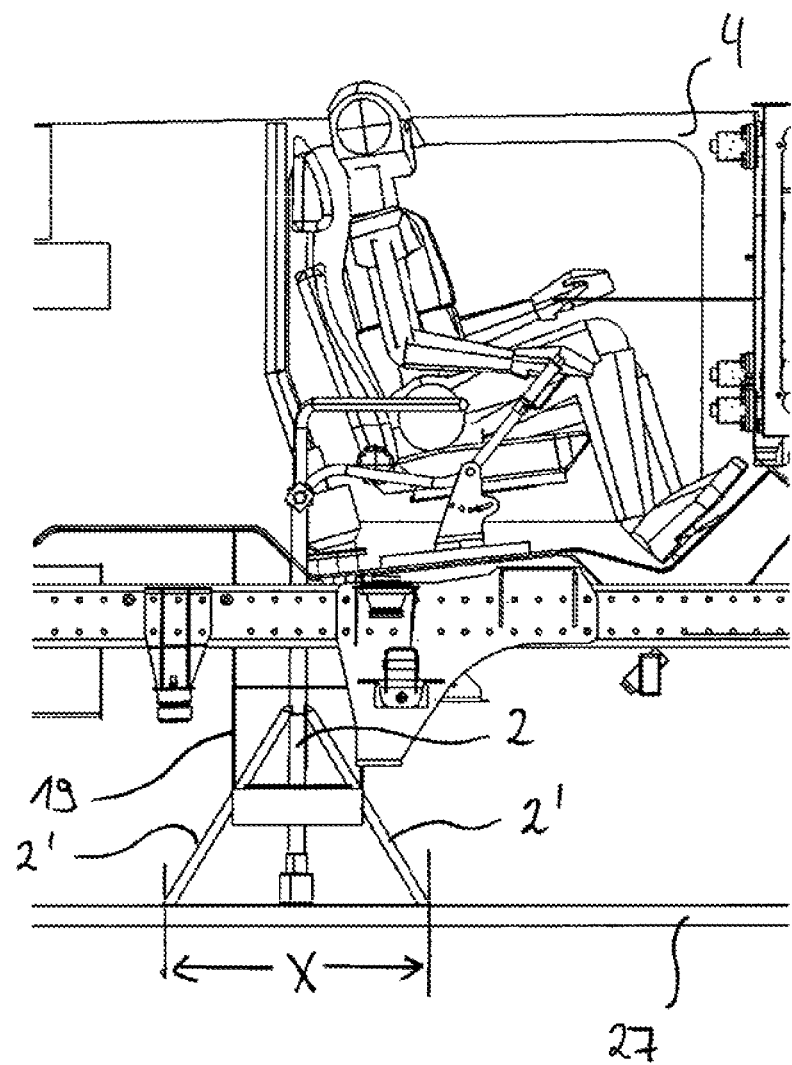
FIG. 8 shows the vehicle of FIG. 4 for explaining the orientation extent.

FIG. 8 shows the schematically illustrated orientation extent X of the sensing probe 2 that can be achieved in the longitudinal direction of the vehicle 4, with the maximum achievable positions of the sensing probe 2' being illustrated.

Figure 9:
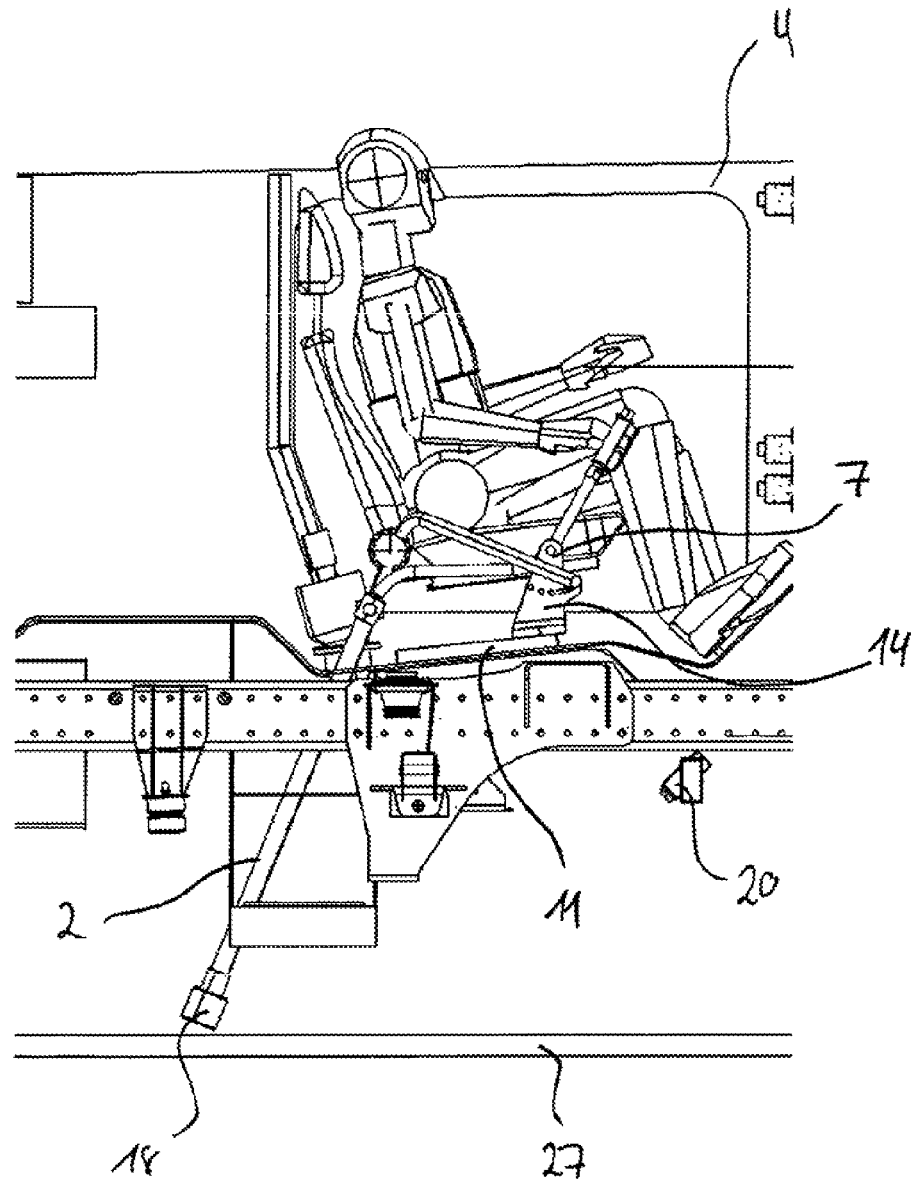
FIG. 9 shows the vehicle of FIG. 8 with the sensing probe oriented toward the rear.

FIG. 9 shows the vehicle 4 in a position of the sensing apparatus 1 in which the sensing probe 2 is oriented toward the rear. For this purpose, the lever support 7, with the bearing bracket and including the apertured plate 14, is shifted toward the front on the linear guide 11 until it reaches an abutment.

Disposed below the vehicle is a camera 20, by means of which the orientation process, and the subsequent sensing process, can be observed by means of a non-illustrated monitor in the vehicle 4.

In a non-illustrated manner, the sensing head 18 is connected to the sensing probe 2 via an articulated joint, since during the ground sensing the sensing head 18 must necessarily be disposed perpendicular to the ground. In this connection, the articulated joint can have a spring-biased configuration. By applying an appropriately great pressure, the detector 21 must in fact ensure that a perpendicular positioning of the sensing head on the ground 27 is achieved.

Figure 10:
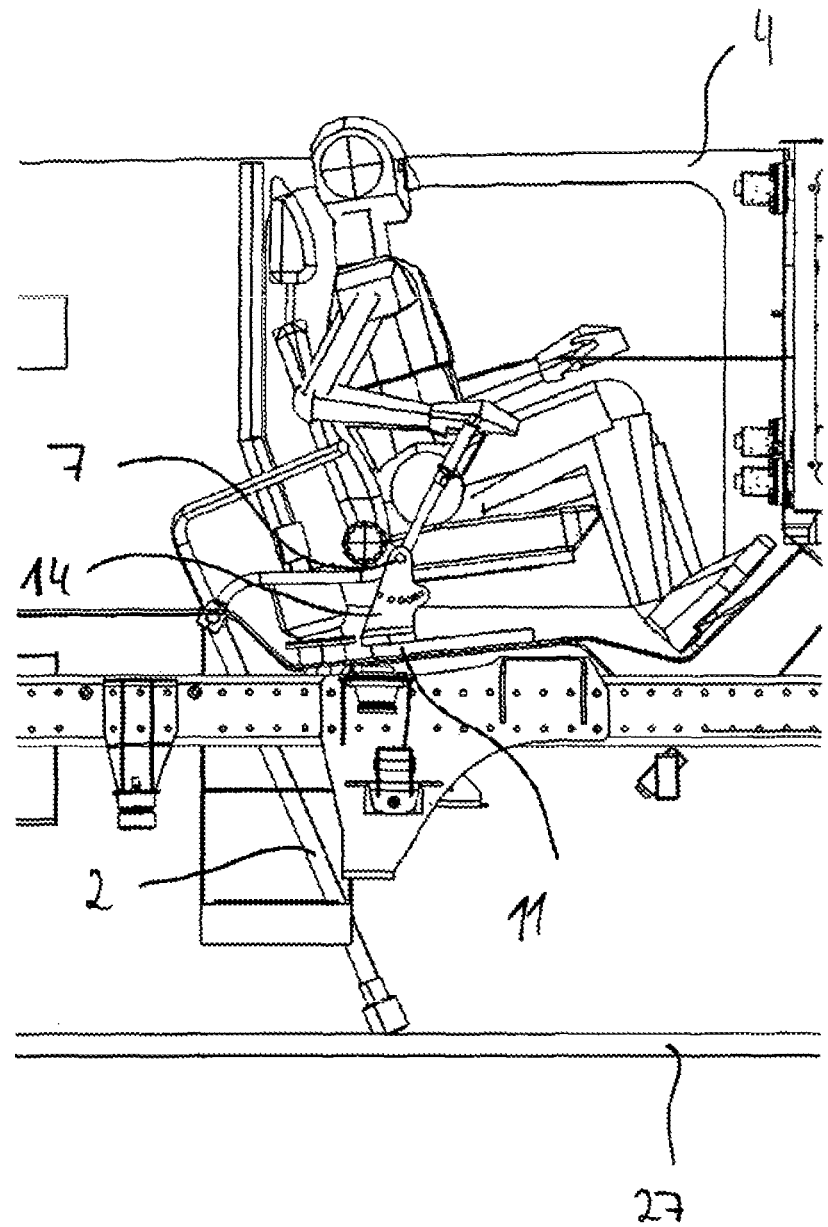
FIG. 10 shows the vehicle of FIG. 8 with the sensing probe oriented toward the front.

FIG. 10 shows the corresponding position with the sensing probe 2 oriented toward the front. For this purpose, the lever support 7, with the bearing block and including the apertured plate 14, is shifted toward the rear on the linear guide 11 until it reaches an abutment.

Figure 11:
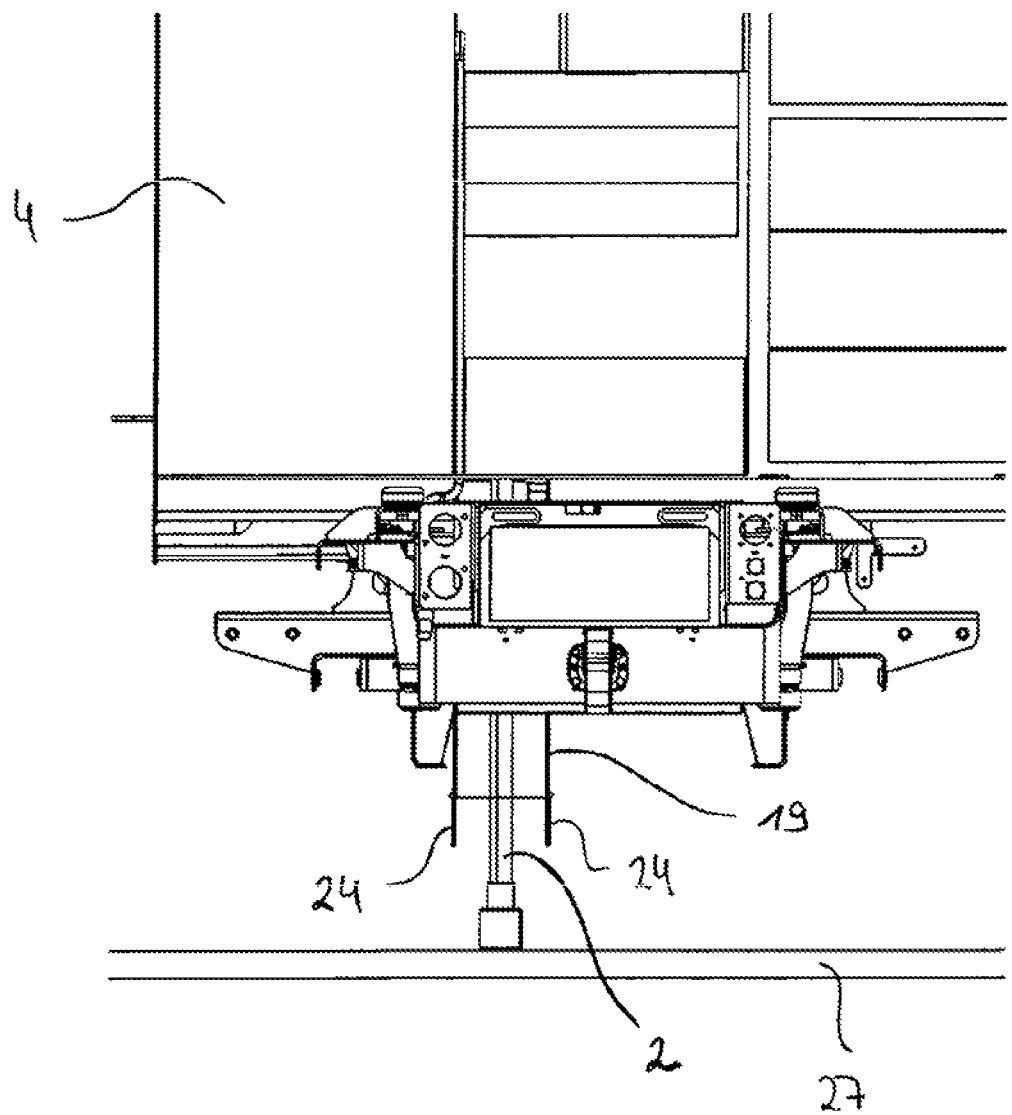
FIG. 11 is a transverse sectional end illustration of the vehicle of FIG. 1.

FIG. 11 shows a rear view of the vehicle 4 with the closure mechanism 24 opened and the sensing probe 2 in the ground sensing position.

Figure 12:
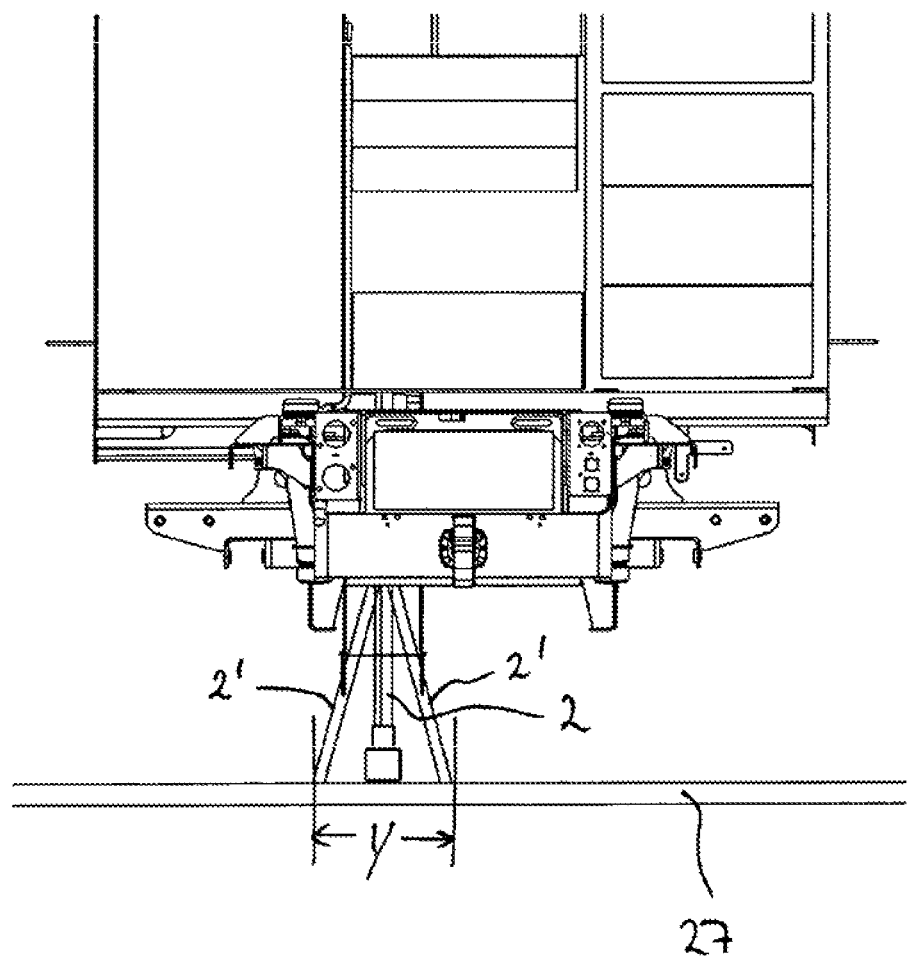
FIG. 12 shows the vehicle of FIG. 11 for explaining the orientation extent.

FIG. 12 shows the lateral orientation extent Y of the sensing probe 2, with the maximum achievable positions of the sensing probe 2' being illustrated.

All together, there results a ground area (X, Y) that can be scanned or probed by the sensing head of about 1 m$^2$.

Figure 13:
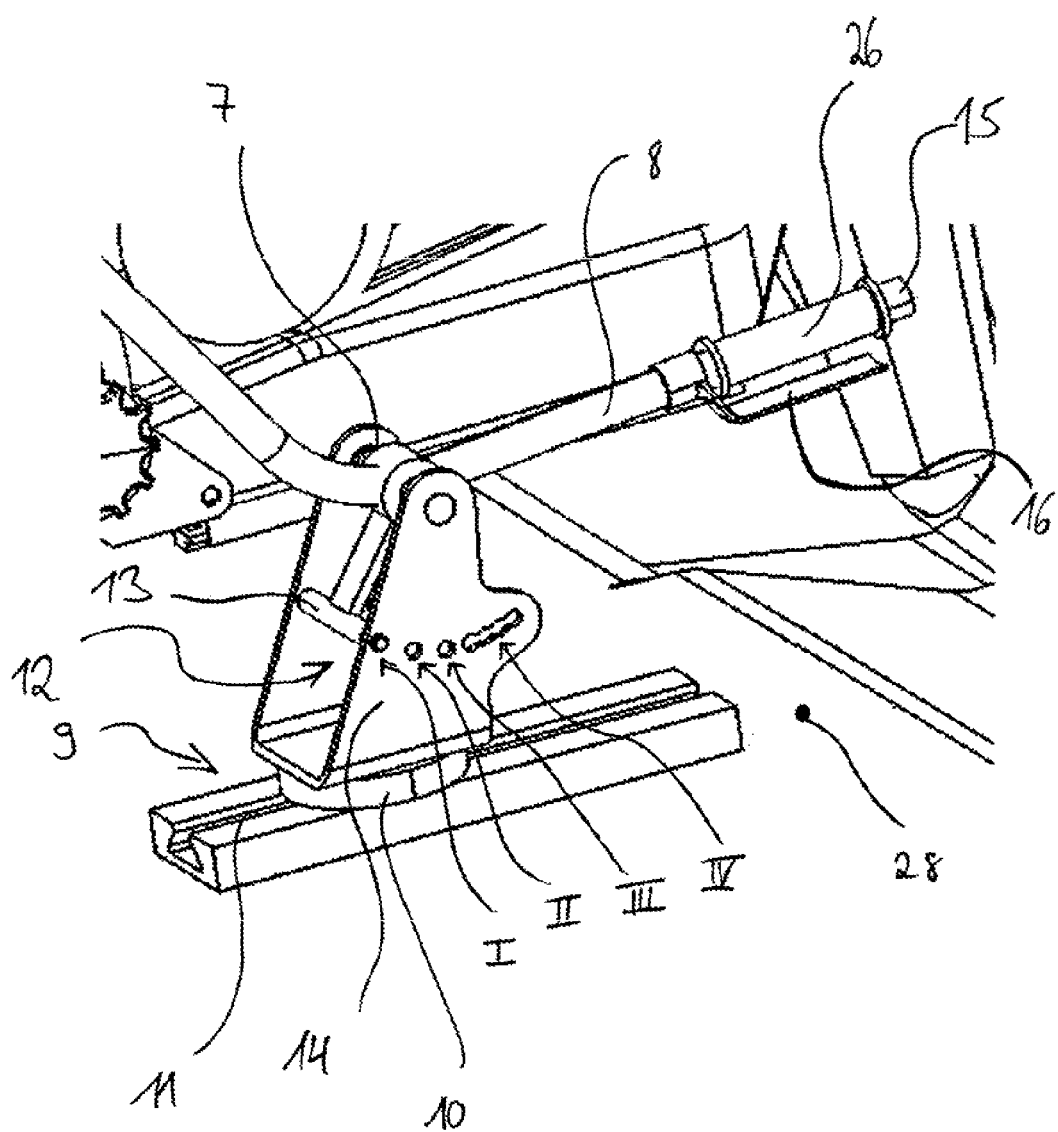
FIG. 13 is an enlarged illustration of the handle of FIG. 6.

FIG. 13 is an enlarged illustration of the handle 3, with a lowering locking mechanism 12 being provided in the region of the lever support 7. The lever support 7, which is configured as a forked apertured plate mechanism 14, cooperates, for locking, with a pin 13 that can engage in various recesses or openings of the apertured plate 14. The pin 13 can be released by a Bowden cable and the lowering release actuation mechanism 15, which is designed as a push button for the thumb.

Associated with the various holes or openings of the apertured plate 14 are various prescribed positions of the sensing probe 2. The opening or aperture I represents the rest or idle position. The opening or aperture II represents the air sensing position. The opening or aperture III represents the head-changing position, which is disposed between the air sensing position and the ground sensing position. The notched slot IV represents the pivot range for the ground sensing position, and serves for height compensation. By means of a fine distribution of the notches, a specific ground sensing position can be locked in by means of the pin 13, the ends of which are embodied as a detent, and which engages the notches of the slot. In a non-illustrated manner, it is also alternatively possible to lock the ground sensing position in an infinitely variable manner by means of a frictional pairing. In both embodiments, the detector 21 can release the handle 3 during the sensing process.

A sensor system can be disposed on the pin 13 or on the apertured plate 14; the sensor system senses the engagement of the pin 13 and thereby the position of the sensing probe 2, so that generation of a signal takes place as a function of the probe status. The appropriate signals can be communicated to the detector or to the driver of the vehicle 4, for example optically or acoustically. In addition, by means of a control device 31 a vehicle interlock can be provided that prevents movement of the vehicle when the sensing apparatus 30 is in the ground sensing position (see FIG. 14).

The handle 3 is furthermore provided with a non-illustrated orientation blocking mechanism, which can be released by the orientation release actuation mechanism 16, which is configured as a draw or pull lever. When the orientation release actuation mechanism is released, a rotational movement of the pivot bearing 10, as well as a linear movement of the horizontal linear guide 11, are possible. When the orientation release actuation mechanism is not activated, an orientation movement is blocked, and a rotation of movement of the pivot bearing 10 as well as a linear movement via the linear guide 11 are not possible.

The orientation release actuation mechanism 16 and the lowering release actuation mechanism 15 are disposed in the region of the grip 26 of the one-hand pull lever 8, so that the entire handle 3, which is disposed in the grasping space or zone of the detector 21 next to the seat 22 of the detector, can be ergonomically and conveniently operated with only one hand.

The specification incorporates by reference the disclosure of German 10 2009 015 828.6 filed Apr. 1, 2009, as well as International application PCT/DE2010/000015 filed Jan. 5, 2010.

The present invention is, of course, in no way restricted to the specific disclosure of the specification and drawings, but also encompasses any modifications within the scope of the appended claims.

LIST OF REFERENCE NUMERALS

1. Sensing Apparatus
2. Sensing Probe
3. Handle
4. Vehicle
5. Ball-and-Socket Joint
6. Pivot Bearing
7. Lever Support
8. Lever
9. Support Bracket Mechanism
10. Pivot Bearing
11. Linear Guide
12. Lowering Locking Mechanism
13. Pin
14. Apertured Plate
15. Lowering Release Actuation Mechanism
16. Orientation Release Actuation Mechanism
17. Tubular Section
18. Sensing Head
19. Compartment
20. Camera
21. Detector
22. Seat
23. Rubber Bellows or Covering
24. Closure Mechanism
25. Corrugated Tube
26. Grip
27. Ground
28. Interior Bottom of Vehicle
29. Support Plate having Ball Insert with a Passage
I Rest or Idle Position
II Air Sensing Position
III Head-Changing Position
IV Ground Sensing Positions
B Base of Vehicle
H Horizontal Pivot Plane
X Orientation Extent in the Longitudinal Direction of the Vehicle
Y Orientation

The invention claimed is:

1. A vehicle having a sensing apparatus for ground sensing from the interior of the vehicle, wherein said sensing apparatus comprises:
   a sampling probe that is capable of being brought into contact with the ground; and
   a handle configured for moving said sampling probe between a raised rest position and a lowered ground sensing position, wherein said sampling probe is guided through a bottom of the interior of the vehicle.

2. A vehicle according to claim 1, wherein said sampling probe is connected to the vehicle by means of a ball insert having a passage therethrough.

3. A vehicle according to claim 1, which further comprises a sampling head, wherein said sampling probe includes a tubular section, and wherein said sampling head is disposed on an end of said tubular section.

4. A vehicle according to claim 3, which further comprises a compartment disposed below the vehicle, wherein said sampling probe is guided through said compartment.

5. A vehicle according to claim 4, wherein said compartment is closable, and wherein in the rest position, said sampling head is disposed in said compartment.

6. A vehicle according claim 1, which further comprises a display device and a camera disposed below the vehicle, wherein a sensing process is observable by the display device.

7. A vehicle according to claim 3, wherein said sensing head is provided with a heating element for the volatilizing a ground sample, and wherein ground sample vapors can be conveyed through said sensing head to an analysis device.

8. A vehicle according to claim 1, wherein a working space for a detector individual is disposed in the interior of the vehicle and wherein said handle is arranged within a grasping zone of the detector individual.

9. A vehicle according to claim 1, which further comprises a sensor for sensing a ground sensing position, wherein said sensor is connected to a control device that, upon sensing the ground sensing position, is configured to prevent movement of the vehicle.

* * * * *